United States Patent [19]
West et al.

[11] Patent Number: 6,148,857
[45] Date of Patent: Nov. 21, 2000

[54] COMBINATION FLUID SUPPLY AND ASPIRATION VALVE ASSEMBLY FOR USE IN MEDICAL PROCEDURES

[75] Inventors: Joe E. West; Garrett L. Barker, both of Meridian, Tex.

[73] Assignee: Valley West, Inc., Meridian, Tex.

[21] Appl. No.: 09/255,351

[22] Filed: Feb. 23, 1999

[51] Int. Cl.[7] .................................................. F16K 11/22
[52] U.S. Cl. ........................... 137/596.2; 604/33; 604/35
[58] Field of Search .......................... 137/596.2; 604/33, 604/35

[56] References Cited

U.S. PATENT DOCUMENTS

| | | |
|---|---|---|
| 4,388,946 | 6/1983 | Richter et al. . |
| 4,456,223 | 6/1984 | Ebling ................................... 604/33 X |
| 4,570,677 | 2/1986 | Roxton et al. . |
| 5,125,910 | 6/1992 | Freitas . |
| 5,188,591 | 2/1993 | Dorsey, III . |
| 5,244,459 | 9/1993 | Hill .......................................... 604/33 |
| 5,303,735 | 4/1994 | Cerola et al. ......................... 137/596.2 |
| 5,334,140 | 8/1994 | Phillips . |
| 5,337,140 | 8/1994 | Hagiwara et al. . |
| 5,348,555 | 9/1994 | Zinnanti ................................ 604/33 X |
| 5,388,612 | 2/1995 | Cerola et al. . |
| 5,391,145 | 2/1995 | Dorsey, 111 . |
| 5,447,494 | 9/1995 | Dorsey, 111 . |
| 5,449,145 | 9/1995 | Wortrich . |
| 5,449,357 | 9/1995 | Zinnanti . |
| 5,490,836 | 2/1996 | Desai . |
| 5,554,112 | 9/1996 | Walbrink et al. . |
| 5,562,640 | 10/1996 | McCabe et al. . |
| 5,573,504 | 11/1996 | Dorsey, 111 . |
| 5,586,977 | 12/1996 | Dorsey ................................... 604/33 X |
| 5,658,249 | 8/1997 | Beland et al. . |
| 5,722,949 | 3/1998 | Sanese . |
| 5,803,510 | 9/1998 | Dorsey ................................... 604/35 X |
| 5,993,410 | 11/1999 | Vincent et al. ......................... 137/33 X |

*Primary Examiner*—Gerald A. Michalsky
*Attorney, Agent, or Firm*—Akin, Gump, Strauss, Hauer & Feld, L.L.P.

[57] ABSTRACT

A combination suction and irrigation fluid supply valve assembly includes a first body part with an axial passage and opposed bosses and second and third body parts mounted on the first body part and supporting respective spool type closure members for controlling flow of irrigation fluid and aspiration of fluids through a medical instrument connected to the valve assembly. The fluid supply closure member includes differential areas to provide for fluid pressure biasing of the closure member in a closed position and the suction closure member includes a substantial groove formed therein to provide unobstructed flow of debris laden fluid through the valve assembly. Connector assemblies are connected to the opposed bosses on the body to provide connection to a medical instrument while minimizing unwanted disconnection from the instrument. Circumferentially spaced grooves on one of the connector assemblies are operable to receive a locating pin on the instrument to provide for predetermined orientation of the instrument. Button type actuators are arranged with respect to a hand grip on the valve body to provide ease of handling and operation by either hand of the valve operator.

22 Claims, 4 Drawing Sheets

COMBINATION FLUID SUPPLY AND ASPIRATION VALVE ASSEMBLY FOR USE IN MEDICAL PROCEDURES

FIELD OF THE INVENTION

The present invention pertains to a manually actuatable combined fluid supply and fluid suction or aspiration control valve assembly for use with medical instruments and procedures.

BACKGROUND

Combination aspiration or suction and fluid delivery or irrigation control valves are known for use in various medical procedures. Such valves are typically used in connection with cannula and endoscopic instruments and may be configured in a manner reminiscent of so-called trumpet valves for ease of manipulation by the person performing the medical procedure.

Although valves of the general type described above are known, there continue to be needs for further improvements in such valves. For example, there has been a continuing need for the development of a valve assembly which is easily manipulated and operated with either hand by the user, greater control over valve position for both the fluid supply valve and the aspiration or suction valve while minimizing operator fatigue, a reduced tendency for the suction or aspiration valve to be clogged by debris passing therethrough and use of the valve in a comfortable and easily controlled position while providing for rotatable indexing of an instrument connected to the valve so that the instrument is also properly positioned.

The above mentioned desiderata in a combination suction or aspiration and irrigation or fluid supply valve, as well as other improvements in such valves, have been substantially met by the present invention.

SUMMARY OF THE INVENTION

The present invention provides an improved combination handheld and hand operated fluid suction or aspiration and fluid supply or irrigation valve for use in medical procedures, in particular.

In accordance with one aspect of the present invention a combination irrigation and aspiration valve is provided which has fluid suction flow path of substantial cross sectional area through the valve assembly to minimize clogging of the valve by debris entrained in the suction fluid.

In accordance with another aspect of the present invention, the configuration of the fluid supply or irrigation valve closure member and actuator is such as to minimize operator fatigue and provide greater control over the metering of fluid flow therethrough. In this regard the closure member of the fluid irrigation fluid control valve is both spring and pressure biased into the closed position and is provided with a combination of housing and closure member construction which provides finer control over metering of fluid flow. Still further, both the suction valve closure member and the irrigation fluid closure member are retained in assembly with their respective valve bodies by an o-ring type seal and retainer, respectively.

In accordance with a further aspect of the present invention a control valve assembly advantageous for use in endoscopic or laproscopic procedures is provided with a connector configuration for connecting the valve to a medical instrument or probe wherein the connector is adapted to positively lock the instrument or probe in a predetermined position relative to the valve structure, requires a relatively small force to insert and remove the probe with respect to the valve body and provides for selectively rotatably indexing the probe with respect to the valve body and closure member actuators so that the user of the valve may hold the valve in a convenient and comfortable position while orienting the instrument or probe in a desired position. Moreover, the connector or retainer structure for supporting and connecting the probe to the valve is designed for use with a wide range of instrument sizes and configurations.

The above-mentioned features and advantages of the present invention together with other important aspects thereof will be further appreciated by those skilled in the art upon reading the detailed description which follows in conjunction with the drawing.

DESCRIPTION OF A PREFERRED EMBODIMENT

In the description which follows, like parts are marked throughout the specification and drawing with the same reference numerals, respectively. The drawing figures are not necessarily to scale and certain features may be shown exaggerated in scale or in somewhat schematic form in the interest of clarity and conciseness.

Figures 1, 2:
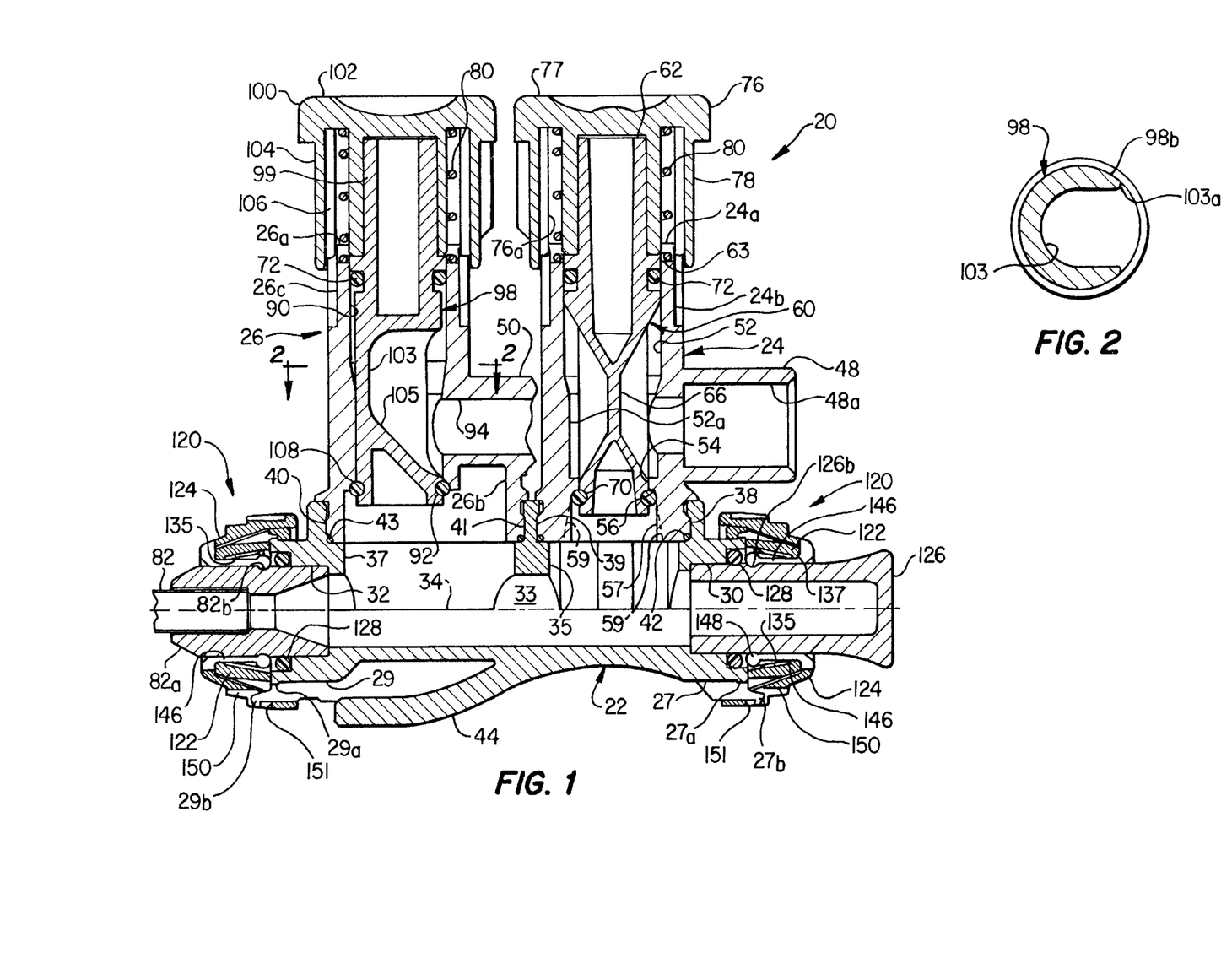
FIG. 1 is a longitudinal central section view of a combination aspiration and fluid supply or irrigation valve in accordance with the present invention.
FIG. 2 is a detail section view taken along the line 2—2 of FIG. 1.
Figure 3:
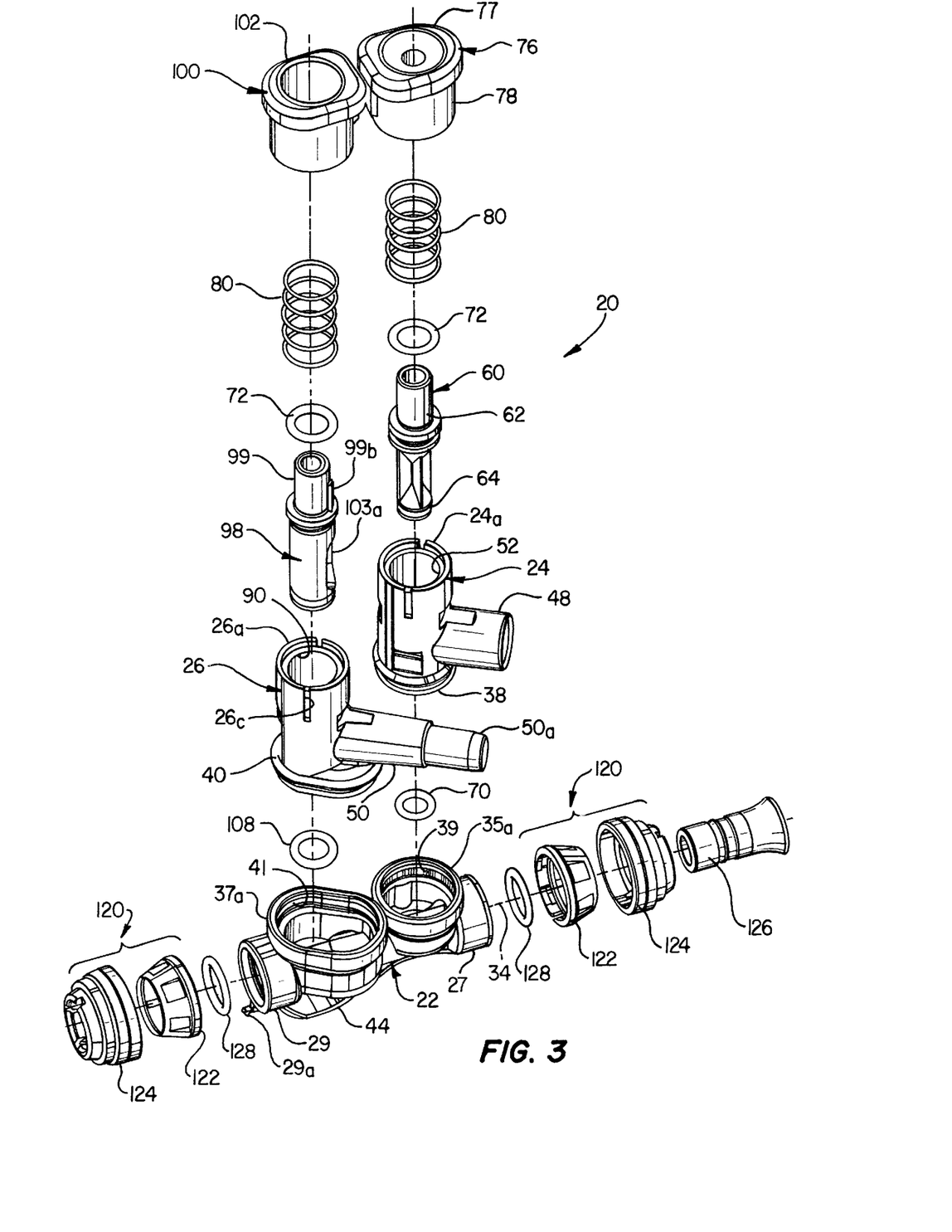
FIG. 3 is an exploded perspective view of the valve shown in FIG. 1.

Referring to FIGS. 1 and 3, there is illustrated a combination suction and fluid supply valve assembly generally designated by the numeral 20. The term suction may also refer to aspiration as used in a medical context and the term fluid supply may also refer to irrigation, also as used in a medical context. The valve assembly 20 is characterized by a molded lower body member 22 and spaced apart upstanding, generally cylindrical body members 24 and 26 which are releasably connectable to the body member 22. The lower body member 22 is provided with opposed, generally cylindrical bosses 27 and 29 which include respective coaxial bores 30 and 32, FIG. 1 opening into a common passage 33 and aligned with each other along a central axis 34, FIG. 1. The passage 33 is intersected by stepped transverse bores 35 and 37, FIG. 1, which receive, respectively, circumferential flanges 38 and 40 of the respective upper body members 24 and 26. The flanges 38 and 40 are snap fittable within circumferential recesses 39 and 41 in the stepped bores 35 and 37, FIG. 1, whereby the upper body members 24 and 26 may be releasably mounted on the lower body member 22 in fluid tight sealing engagement therewith and provided by o-ring seal members 42 and 43, FIG. 1.

As shown in FIGS. 1 and 3, the lower body member 22 is provided with a contoured finger grip or rest portion 44 integrally molded therewith. As shown in FIG. 3, the body member 22 includes respective cylindrical and oval bosses 35a and 36a which define the grooves 39 and 41 for receiving the flanges 38 and 40 of the respective body members 24 and 26. In such an orientation, as shown, the body member 24 includes a fluid inlet boss 48 formed thereon and the body member 26 includes a fluid suction or aspiration boss 50 formed thereon and wherein these bosses extend at an angle of about 30° to the axis 34 when the body members 24 and 26 are assembled to the body member 22.

Referring further to FIG. 1, the boss 48 defines a fluid inlet port 48a which may be suitably connected to a flexible fluid conduit, not shown, to supply pressure fluid to the valve assembly 20. The body member 24 is also provided with an elongated stepped longitudinal bore including a first bore 52 which is tapered to a portion 52a which extends to a reduced diameter bore 54 defining a valve seat 56. Bore 52 opens to the upper distal end 24a of the body member 24, see FIG. 3 also. As shown in FIG. 1, the valve seat 56 delimits one end of a bore 57 opening into passage 33. Bore 57 is intersected by a plurality of circumferentially spaced axially extending tapered grooves 59 which taper radially inwardly toward the valve seat 56.

Referring further to FIGS. 1 and 3, the valve body member 24 is adapted to support an elongated spool type fluid supply valve closure member 60, including an upwardly extending generally cylindrical head portion 62, a lower generally cylindrical closure portion 64 and a generally recessed area 66 disposed between the portions 62 and 64 to allow fluid flow to pass the closure member between the port 48a and the passage 33. Circumferential o-ring seals 70 and 72 are releasably retained in suitable grooves formed in the closure member 60. The o-ring 70 is engageable with the valve seat 56 to form a fluid tight closure and to retain the closure member 60 in the stepped bore 52, 54 of the body member 24.

The closure member 60 is suitably connected to a contoured actuator button 76 which includes a thumb or finger pad 77 preferably molded integral with a generally cylindrical tubular body portion 78. The body 78 is adapted to be sleeved over the distal end 62 of the closure member 60 and suitably secured thereto with a coil biasing spring 80 interposed the distal end 24a of the body member 24 and the pad 77, as shown in FIG. 1. One or more elongated key portions 76a, FIG. 1, are axially slidable in cooperating grooves 24b formed in the body member 24 to orient the contoured pad 77 and closure member 60 properly with respect to the valve body members 22 and 24. Accordingly, the closure member 60 is spring biased into the valve closed position of the fluid supply or irrigation valve portion of the valve assembly 20.

Moreover, the diameter of closure member body portion 63, FIG. 1, which is dimensioned to be snug fitting but axially slideable in the bore 52 is greater than the diameter of the closure member part 64 which is dimensioned to be snug fitting but slidable in the bore 54. Accordingly, a differential cross sectional area is exposed to fluid flowing into the bore 52 from the port 48a which exerts a pressure biasing force on the closure member 60 to bias same to the closed position. The combined effect of the spring bias acting on the closure member 60 and pressure bias acting thereon together with the tapered grooves 59 which intersect the bore 57 provide for fine digital control of metering fluid flow through the valve assembly 20, including the passage 33, to a suitable instrument connected to the valve, such as shown in FIG. 1 wherein a hollow tubular fluid conducting instrument or cannula 82 is adapted to conduct fluid from the passage 33 to the opposite end of the cannula, not shown, for performing a medical procedure.

Referring still further to FIGS. 1 and 3, the body member 26 is also provided with a slightly tapered cylindrical bore 90 extending from an upper distal end 26a to a lower cavity 26b in the body member, FIG. 1, and defining a valve seat 92. A fluid suction or aspiration port 94 extends through the boss 50 and opens into the bore 90. An elongated tubular closure member 98 is adapted to be disposed in the bore 90 and includes an upper reduced diameter tubular end portion 99 engageable with a digital actuator button 100 substantially similar to the button 77 and including a contoured head portion 102 adapted to be digitally actuated and complementary to the contour of the head portion 77 of the actuator button 76.

The closure member 98 includes a longitudinally extending deep groove 103, see FIG. 2 also, having a sloped bottom wall 105 and intersecting the outer diameter 98b of the closure member at a port 103a, FIG. 2, which faces the port 94 to provide a flow path between the port 94 and the passage 33 via the cavity 26b which is substantially unobstructed and permits the flow of debris laden fluids from the cannula 82 through the passage 33, the cavity 26b, the groove 103 into the port 94 when the closure member 98 is in a valve open position.

The actuator button 100 is suitably mounted on the distal end part 99 of the closure member 98 and is provide with a tubular body portion 104 having one or more suitable longitudinally extending key portions 106 adapted to be slidable in one or more grooves 26c extending axially along the body 26, as shown, to orient the closure member 98 and the actuator button 100 in a preferred direction. The closure member 98 is retained in the bore 90 by a circumferential o-ring type seal 108 retained in a suitable groove in the lower end part of the closure member 98, as shown, and engageable with the valve seat 92 to form a fluid tight seal between the groove 103, bore 90 and the cavity 26b when the closure member is in a valve closed position. A second o-ring seal 72 is retained in a groove on the closure member 98 in the same manner that the first mentioned o-ring seal 72 is retained on the closure member 60. Accordingly, the closure member 98 is also biased into the closed position by a coil spring 80 engageable with the actuator button 100 and the valve body 26, as illustrated.

As shown in FIG. 3, the closure member 98 includes an axially extending key 99b formed on the upper tubular end 99 which is adapted to extend in engagement with a corresponding keyway, not shown, formed in the actuator button 100 to orient the closure member with respect to the actuator button. Accordingly, since the actuator button 100 is oriented with respect to the body member 26 by the cooperating key and keyway portion 106 and 26c, the closure member 98 is properly oriented with respect to the port 94 when assembled to the body member 26 so that the groove 103 is in full registration with the port 94 and provides maximum fluid flow passage space for debris laden fluid flowing from the passage 33 and cavity 26b into the groove 103 and out of the valve assembly 20 through the port 94. A suitable suction conduit, not shown, is adapted to be connected to the boss 50 at a spigot portion 50a, FIG. 3, in a conventional manner.

Those skilled in the art will appreciate that when the closure member 98 is fully depressed by engagement of the actuator button 100 and moving same axially downwardly, viewing FIG. 1, in a direction normal to the axis 34, that a substantial flow path is provided through the closure member between the passage 33 and the port 94 to minimize clogging of the valve assembly when debris laden fluid is being aspirated through the cannula 82 and the valve assembly 20. The closure member 98 is retained in assembly with the body 26 by the O-ring seal 108 in the same manner that the closure member 60 is retained in assembly with the body 24.

Those skilled in the art will recognize from the foregoing description of the valve assembly 20 that the valve assembly including the body members 22, 24 and 26 together with the actuator buttons 76 and 100 provides an easily manipulated and operated combination suction and fluid supply valve which is particularly adapted for use in medical procedures to conduct fluids through a cannula or the like, such as the cannula 82, in both directions. The orientation of the body members 24 and 26, together with the bosses 48 and 50 which define the fluid flow ports, and the grip 44, together with the actuator button 76 and 100, are configured to provide for ease of operation of the valve assembly with either hand. Still further, as previously mentioned, the spring and pressure fluid biased closure member 60 in combination with the flow passages provided by the tapered grooves 59 provides for precise metering of fluid from the port 48a the passage 33 when fluid is being supplied to the cannula 82 or other medical instrument attached to the valve assembly 20.

The valve assembly 20 is preferably constructed of medical grade plastic materials and is configured to be operable at relatively high pressures as great as fifty psig to seventy psig. The closure member 60 in cooperation with the body 24 is operable to be held closed with a greater force as fluid supply pressure increases due to the differing areas of the valve seat with respect to the cross sectional area provided by the body part 63 of the closure member 60. This arrangement provides for use of a closure spring 80 having a lower spring rate which means there is less force required by the operator to hold the closure member 60 in a valve open position under most operating conditions. Moreover, as mentioned previously, the tapered metering grooves 59 allow operation of the valve closure member 62 to control flow of fluid with greater sensitivity, ranging from droplets to full flow.

Another significant advantage of the valve assembly 20 is the provision of improved connectors for accommodating cannulas and other medical instruments of relatively different diameters and configurations. Referring again to FIGS. 1 and 3, the cylindrical boss portion 27 of the body member 22 includes a circumferential flange 27a and an axially extending retaining finger 27b integrally formed thereon. In like manner, the cylindrical boss 29 includes a circumferential flange 29a and an axially extending retaining finger 29b integrally formed thereon. Each of the bosses 27 and 29 is adapted to support a connector assembly 120 including a generally frusto conical shaped hub member 122 and an instrument retainer member 124, respectively. A removable generally cylindrical plug 126 may be retained connected to the boss 27 by the connector assembly 120, FIG. 1, and is in fluid-tight sealing engagement with the boss by an o-ring seal 128 retained in a suitable groove intersecting the bore 30 and engageable with the outer diameter of the plug 126. In like manner, as shown in FIG. 1, the cannula 82 has a cylindrical hub 82a which is adapted to be disposed in the bore 32 and in fluid-tight engagement with an o-ring seal 128, also retained in a groove intersecting the bore 32, as shown. The cannula 82 and the plug 126 may be replaced by a suitable medical instrument which includes a hub portion, not shown in FIG. 1, and an axially extending portion which extends through the passage 33 and the bore 32 for use in certain medical procedures and as will be described in further detail herein.

Figures 9, 10:
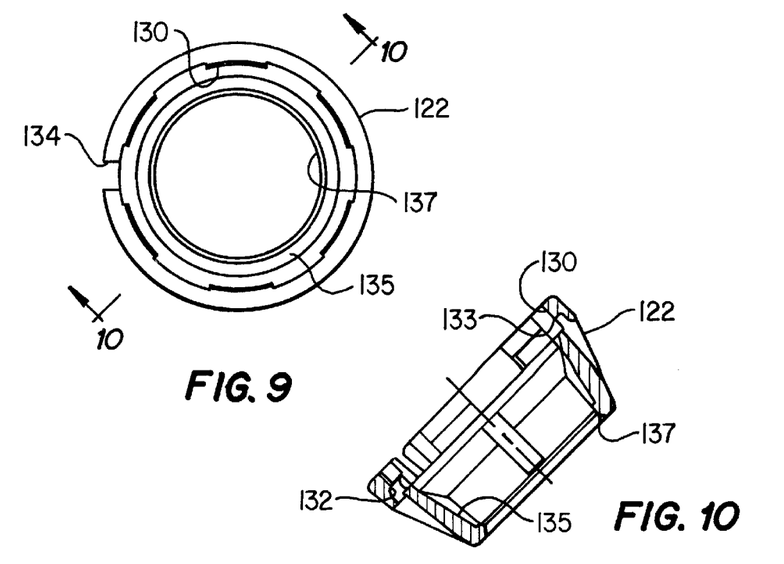
FIG. 9 is an end view of a retainer hub for the connector assembly for the valve of FIG. 1.
FIG. 10 is a section view taken generally along the line 10—10 of FIG. 9.

Referring further to FIG. 1, and also FIGS. 9 and 10, the retainer hub 122 includes a circumferential bore 130 intersecting an enlarged bore portion 132, FIG. 10, and defining a circumferential collar 133 which is engageable with the flange 27a or 29a to retain the hub 122 in assembly with the bosses 27 or 29. An axial slot 134, FIG. 9, intersects the bore 130 to provide clearance for the retaining finger 27b or 29b when the hub 122 is assembled to the boss 27 or 29, as shown in FIG. 1. The retainer hub 122 is also provided with a frustoconical inner wall 135, FIG. 10, tapered from the bore 130 to a reduced diameter bore 137.

Figures 7, 8:
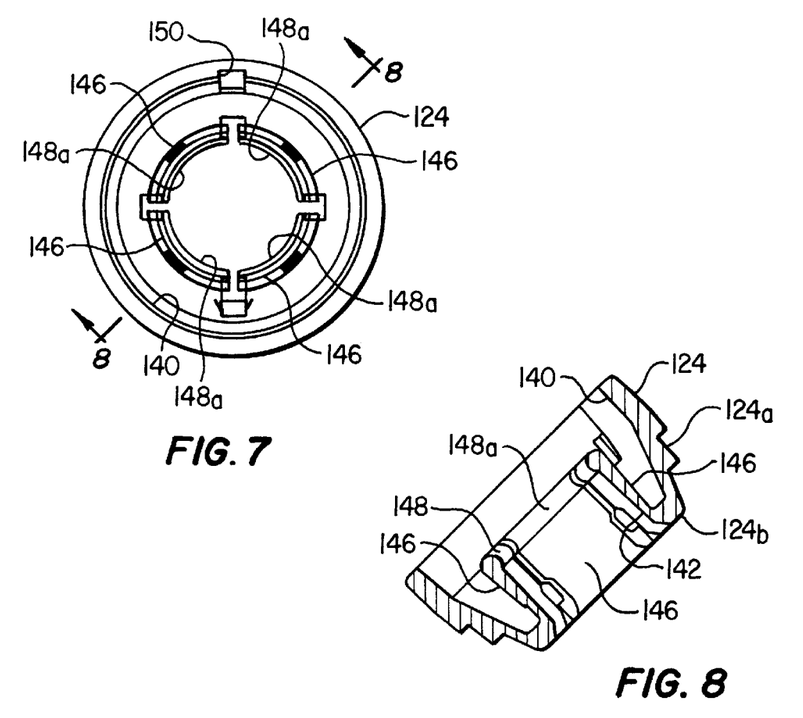
FIG. 7 is an end view of the probe retainer member of the connector assembly for the valve shown in FIGS. 1 and 3.
FIG. 8 is a section view taken along the line 8—8 of FIG. 7.

Referring now to FIGS. 7 and 8, the retainer member 124 is characterized by a generally cylindrical member having an enlarged diameter bore 140 at one end and an axially stepped outer surface 124a to facilitate digital engagement of the retainer member. A reduced diameter bore 142 formed by four circumferentially spaced axially extending and radially deflectable fingers 146. The fingers 146, together, form a substantially circumferential reentrant retaining collar 148, FIGS. 7 and 8, formed by respective collar portions 148a on each of the fingers 146. The fingers 146 are radially deflectable outwardly to allow disengagement of the collar 148 from the plug 126, for example, see FIG. 1. In this regard, the plug 126 is preferably formed with a circumferential groove 126b registrable with the collar portions 148a of the respective fingers 146 to releaseably retain the plug in the bore 30 in fluid-tight sealing engagement with the o-ring 128.

In like manner, viewing FIG. 1 the hub portion 82a of the cannula 82, is provided with a circumferential groove 82b for retaining the hub in assembly with the connector 120 mounted on boss 29 by engagement with the radially deflectable fingers 146 at the collar portions 148a of each finger. If it is attempted to remove either the cannula 82 or the plug 126 from the connectors 120, respectively, by axially pulling these members away from the connectors and out of the bores 30 or 32, the fingers 146 will engage the sloped wall 135 of the retainer hubs 122 to prevent radial outward displacement of the fingers 146 thereby refusing disengagement of the collar portions 148a from the grooves 126b or 82b, as the case may be. However, if the connector retainer members 124 are pushed axially toward the bosses 27 or 29 while at the same time the plug 126 or the cannula 82 is grasped and moved axially in a direction out of the bores 32 or 34, the fingers 146 may be deflected radially outwardly out of the circumferential grooves 126b or 82b to allow the members 126 or 82 to be released from the connectors, respectively. Of course, the hubs 122 are retained on the bosses 27 and 29 as previously described by engagement of the flanges 27a or 29a with the cooperating flanges 133 on the retainer hubs. The retainer members 124 are retained on the bosses 27 or 29 by the respective fingers 27b or 29b which are disposed in axial slots 150, FIGS. 1 and 7, formed in the retainer members 124 and engageable with an edge surface 151 delimiting the slots 150, as shown in FIG. 1.

Figures 4, 5:
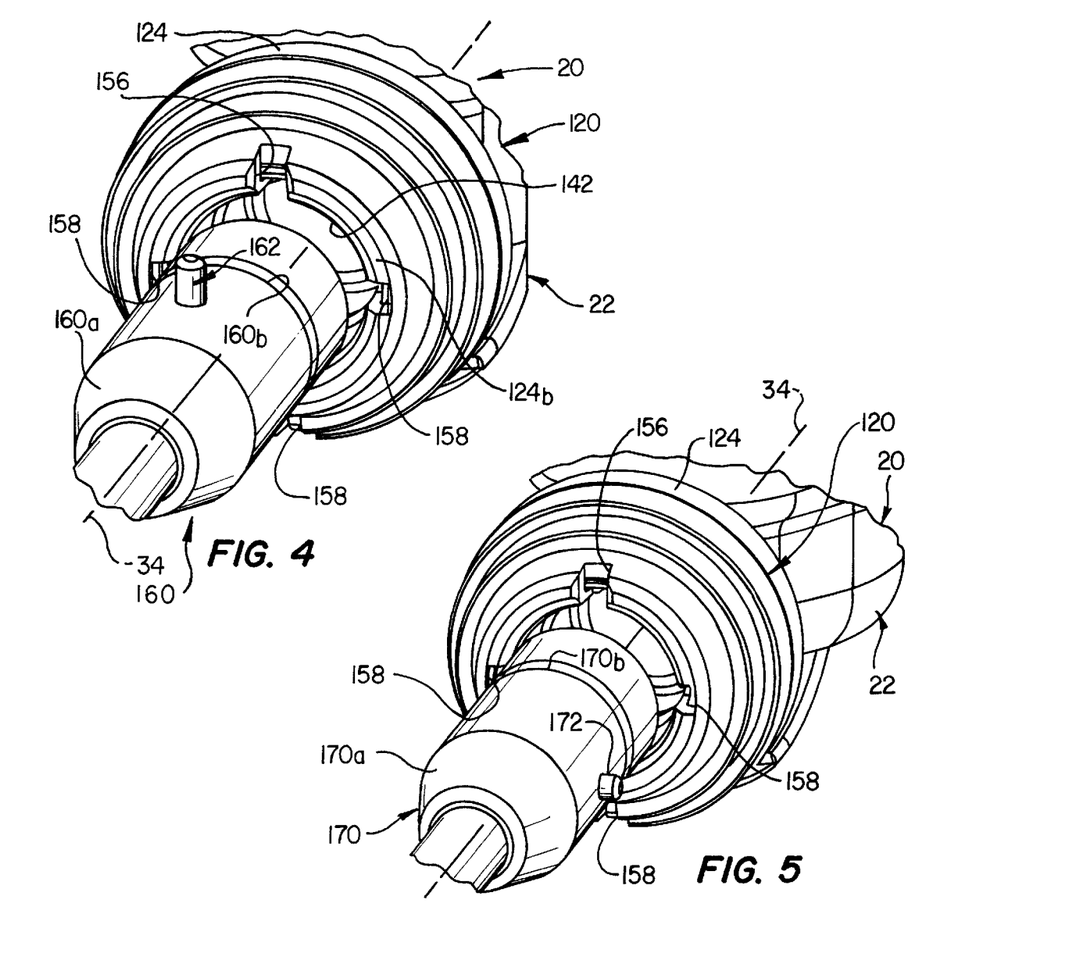
FIG. 4 is a detailed perspective view of one of the medical instrument or probe connector and retainer assemblies.
FIG. 5 is a view similar to FIG. 4 showing a probe oriented in a second position.

Referring now to FIGS. 4 and 5, another advantage of the connectors 120 is illustrated wherein the connector retainer member 124 is provided with four circumferentially spaced axially extending grooves 156 and 158. The groove 156 has a radial extent with respect to the axis 34 which is greater than the grooves 158. Each of the grooves 156 and 158 opens to the bore 142 and intersects an end face 124b of the retainer member 124. The groove 156 is disposed opposite the slot 150 so that when the retainer member 124 is mounted on the body member 22 the groove 156 is in a predetermined position. In this way when a medical instrument, such as the instrument 160, FIG. 4, is desired to be used with the valve assembly 20, the instrument 160 includes a hub portion 160a with a radially extending locating pin 162 formed thereon and registrable in the groove 156 but not in the grooves 158. Thus, the instrument 160 is adapted to be oriented only in one position relative to the valve assembly 20.

Alternatively, a medical instrument 170, see FIG. 5, may be provided having a hub portion 170a and a locating pin 172 which is of lesser radial extent than the locating pin 162 of the instrument 160 whereby the instrument 170 may be oriented in one of four equally displaced positions about the axis 34 by positioning the pin 172 in any one of the grooves 156 or 158. As shown in FIGS. 4 and 5, each of the hub portions 160a and 170a is provided with a circumferential groove 160b and 170b, respectively, for registration with the collar 148 to retain the instruments connected to the valve assembly 20, respectively, except when the connector retainer member 124 is purposely moved to release engagement between the instrument hubs and the fingers 146.

Figure 6:
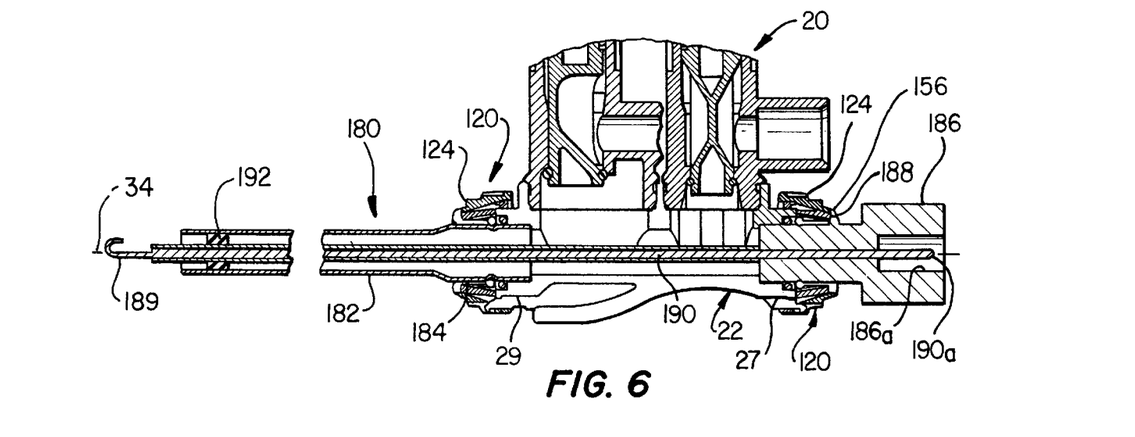
FIG. 6 is a section view similar to FIG. 1 showing a medical instrument or probe mounted in the valve assembly.

Referring briefly to FIG. 6, there is illustrated the valve assembly 20 connected to a medical instrument 180 including an elongated tubular cannula member 182 which is adapted to be releaseably connected to the valve assembly at one of the connector assemblies 120 and includes a hub portion 184 registrable with the connector retainer member 124 in the manner described above for the connection between the hub 82a and the connector member 124. The medical instrument 180 may comprise a electrosurgical instrument including a hub member 186 of electrically nonconductive material and having a locating pin 188 formed thereon for engagement with a retainer member 124 by registration in groove 156 to orient a probe member 189 in a predetermined position with respect to the valve assembly 20. The probe member 189 includes an elongated stem 190 extending through the valve body 22, as shown, and supported with respect to the cannula tube 182 by spaced apart fluted centering members 192 which permit the flow of fluids through the cannula 182 in both directions. The hub 186 includes a center bore 186a which permits an electrosurgical connector, not shown, to be connected to the stem 190 at a distal end 190a.

Accordingly, FIG. 6 illustrates how an instrument 180 may be suitably connected to the valve assembly 20 and a probe 189 oriented in a predetermined position with respect to the valve assembly about central axis 34 so that the operator of the instrument 180 will know its orientation while being able to operate the valve assembly 20 to provide irrigation and aspiration operations. The instrument 180 may, of course, be rotated and angularly oriented at 90° intervals while keeping the valve assembly 20 oriented toward proper grasping and operation and while still keeping a visible relationship between the valve assembly and the instrument. Again, thanks to the connector assemblies 120, the cannula 182 and the hub 186 are retained in fluid-tight connection with the valve assembly 20 until the connector retainer members 124 are purposely axially moved toward the bosses 27 and 29 to allow release of the hub 186 or the cannula 182 from engagement with the valve assembly. Otherwise, the tendency for either one of the cannula 182 or the hub 186 to be moved axially, without first moving the connector retainer members 124, as described above, will result in nonrelease of the cannula or the hub 186 from the valve assembly, which is a desired feature.

Those skilled in the art will appreciate from the foregoing description that an improved combination suction and fluid supply or irrigation valve assembly is provided by the present invention. The valve assembly 20 including the connector assemblies 120 provide several desirable features in applications for use in medical procedures, in particular. As mentioned previously, the valve assembly 20 may be constructed of injection molded plastic parts of medical grade and the components not otherwise identified herein with regard to construction and material may be made using conventional engineering practices and materials compatible with the application, including, medical procedures. Although a preferred embodiment of a valve assembly in accordance with the invention has been described in detail herein. Those skilled in the art will recognize that various substitutions and modifications may be made without departing from the scope and spirit of the appended claims.

What is claimed is:

1. A combination fluid supply and suction valve assembly comprising:
   a body including a passage formed therein and a connector assembly for releasably connecting said body to an instrument including a flow passage in said instrument;
   a first closure member supported on said body for movement between a valve open position and a valve closed position for conducting pressure fluid from a fluid supply port to said passage in said body, said first closure member including a first portion of a diameter greater than a second portion, said second portion including means registrable with a valve seat on said body and providing a net effective area to be acted on by pressure fluid entering said pressure fluid supply port to bias said first closure member toward a closed position;
   a manual actuator member connected to said first closure member for moving said first closure member from a closed position toward an open position to supply fluid through said body to said passage in said instrument; and
   a second closure member supported on said body for movement between a valve open position and a valve closed position and operable to place said passage in said body in fluid flow communication with a suction port, said second closure member being connected to an actuator for moving said second closure member toward a valve open position.

2. The valve assembly set forth in claim 1 wherein:
   said first closure member comprises a spool member retained in said body by a circumferential seal member engageable with said valve seat.

3. The valve assembly set forth in claim 2 including:
   a spring engageable with one of said first closure member and said actuator for said first closure member and for biasing said first closure member in a valve closed position.

4. The valve assembly set forth in claim 3 wherein:
   said body includes a first body part including said passage and a second body part including a stepped bore formed therein for receiving said first closure member.

5. The valve assembly set forth in claim 1 wherein:
   said second closure member includes a generally cylindrical spool member slidably disposed in said body for movement between a valve open position and a valve closed position, said second closure member including a deep groove formed in said spool member opening to a side of said spool member and registrable with said suction port in said body and with said passage in said body in a valve open position to provide an unobstructed flow path between said passage in said body and said suction port.

6. The valve assembly set forth in claim 5 wherein: said second closure member includes a circumferential seal member mounted thereon and engageable with a valve seat formed in said body for retaining said second closure member in assembly with said body.

7. The valve assembly set forth in claim 6 including: an actuator connected to said second closure member and a spring interposed said actuator and said body for biasing said second closure member in a valve closed position.

8. The valve assembly set forth in claim 7 wherein: said body includes a first body part including said passage and a second body part including a bore for receiving said second closure member, said body parts being releasably engageable with each other.

9. A combination fluid supply and suction valve assembly comprising:
a body including a passage formed therein and a connector assembly for releasably connecting said body to a medical instrument including a flow passage in said instrument, said body includes opposed bosses formed thereon, an axial passage extending between said bosses and opposed bores formed in said bosses for receiving a hub portion of said instrument, at least one of said bosses on said body is adapted to support said connector assembly;
said connector assembly includes a generally cylindrical retainer hub mounted on said one boss and a retainer member mounted on said retainer hub, said retainer member including a plurality of radially deflectable fingers formed thereon and releaseably engageable with said hub portion of said instrument;
a first closure member supported on said body for movement between a valve open position and a valve closed position for conducting pressure fluid from a fluid supply port to said passage in said body;
a manual actuator member connected to said first closure member for moving said first closure member from a closed position toward an open position to supply fluid through said body to said passage in said instrument; and
a second closure member supported on said body for movement between a valve open position and a valve closed position and operable to place said passage in said body in fluid flow communication with a suction port, said second closure member being connected to an actuator for moving said second closure member toward a valve open position.

10. The valve assembly set forth in claim 9 wherein: said fingers of said retainer member are engageable with said retainer hub when moved in one direction to prevent radial deflection of said fingers to release said hub portion of said instrument, said retainer member being operable to be moved in an opposite direction to permit radial deflection of said fingers to release engagement with said hub portion of said instrument.

11. The valve assembly set forth in claim 10 wherein: said retainer hub includes a frustoconical surface formed thereon and engageable with said fingers of said retainer member to prevent radial displacement of said fingers to disengage from said hub portion of said instrument.

12. The valve assembly set forth in claim 9 wherein: said retainer hub includes a circumferential flange engageable with a cooperating flange on said boss on said body.

13. The valve assembly set forth in claim 9 wherein: said body includes connector assemblies mounted on each of said bosses, respectively.

14. The valve assembly set forth in claim 9 wherein: said retainer member includes circumferentially spaced axially extending grooves formed therein for engagement with a locating pin disposed on said hub portion of said instrument for orienting said hub portion of said instrument in a predetermined position with respect to said valve assembly.

15. The valve assembly set forth in claim 14 wherein: at least one of said grooves has a radial extent greater than the other of said grooves for locating a hub portion of said instrument in only one position with respect to said valve assembly.

16. A combination fluid supply and suction valve assembly comprising:
a body including opposed bosses and a passage formed therein, at least one of said bosses on said body is adapted to support a connector assembly for releasably connecting a medical instrument to said valve assembly and in flow communication with said passage in said body;
a first closure member supported on said body for movement between a valve open position and a valve closed position for conducting pressure fluid from a fluid supply port to said passage in said body;
an actuator connected to said first closure member for moving said first closure member from a closed position toward an open position to supply fluid through said body;
a second closure member supported on said body for movement between a valve open position and a valve closed position and operable to place said passage in said body in fluid flow communication with a suction port, said second closure member being connected to an actuator for moving said second closure member toward a valve open position; and
a connector assembly including a generally cylindrical retainer hub mounted on said one boss and a retainer member mounted on said retainer hub, said retainer member including a plurality of radially deflectable fingers formed thereon and releaseably engageable with a hub portion of said medical instrument.

17. The valve assembly set forth in claim 16 wherein: said fingers of said retainer member are engageable with said retainer hub when moved in one direction to prevent radial deflection of said fingers to release said hub portion of said instrument, said retainer member being operable to be moved in a opposite direction to permit radial deflection of said fingers to release engagement with said hub portion of said instrument.

18. The valve assembly set forth in claim 16 wherein: said retainer hub includes a circumferential flange engageable with a cooperating flange on said boss on said body.

19. The valve assembly set forth in claim 16 wherein: said retainer member includes one or more circumferentially spaced axially extending grooves formed therein for engagement with a locating pin disposed on said hub portion of said instrument for orienting said hub portion of said instrument in a predetermined position with respect to said valve assembly.

20. A combination fluid supply and suction valve assembly comprising:

a first body part including a fluid flow passage formed therein and means for connecting said first body part to an instrument;

a second body part connectable to said first body part and including a bore for receiving a first closure member in axially slidable relationship therein, said first closure member including a first portion of a diameter greater than a second portion, said second portion including means engageable with a valve seat on said second body part and providing a net effective area to be acted on by pressure fluid entering said valve assembly to bias said first closure member to a valve closed portion;

a third body part connectable to said first body part and including a bore for receiving a second closure member in axially slidable relationship therein;

actuators supported on said second body part and said third body part, respectively, for actuating said first and second closure members, respectively; and a grip portion on said first body part and disposed opposite said actuators to provide for grasping said valve assembly with one hand and operating respective ones of said actuators with said one hand.

21. The valve assembly set forth in claim 20 wherein:

said second body part includes a bore therein adjacent said valve seat and a plurality of tapered grooves extending axially in said bore and intersecting said bore and cooperable with said first closure member for metering fluid flow through said valve assembly.

22. A combination fluid supply and suction valve assembly comprising:

a first body part including a fluid flow passage formed therein and means for connecting said first body part to an instrument;

a second body part connectable to said first body part and including a bore for receiving a first closure member in axially slidable relationship therein;

a third body part connectable to said first body part and including a bore for receiving a second closure member in axially slidable relationship therein, said second closure member including a generally cylindrical spool member slidably disposed in said bore in said third body part and a deep groove opening to one side of said spool member of said second closure member for communicating debris laden fluid through said valve assembly;

actuators supported on said second body part and said third body part, respectively, for actuating said first and second closure members, respectively; and a grip portion on said first body part and disposed opposite said actuators to provide for grasping said valve assembly with one hand and operating respective ones of said actuators with said one hand.

* * * * *